United States Patent [19]

Marteny

[11] Patent Number: 4,911,017
[45] Date of Patent: Mar. 27, 1990

[54] MULTIPLE SAMPLE AUTOMATED CUT GROWTH ANALYSIS

[75] Inventor: Perry Marteny, Stow, Ohio

[73] Assignee: The Goodyear Tire & Rubber Company, Akron, Ohio

[21] Appl. No.: 341,354

[22] Filed: Apr. 21, 1989

[51] Int. Cl.$^4$ ............................................. G01N 19/08
[52] U.S. Cl. ........................................ 73/799; 73/809
[58] Field of Search ................. 73/799, 800, 826, 827, 73/828, 830, 831, 834, 835, 837, 808, 809, 810, 811, 812, 813, 814, 815

[56] References Cited

U.S. PATENT DOCUMENTS

| | | | |
|---|---|---|---|
| 3,803,907 | 4/1974 | Ryckman et al. | 73/800 |
| 3,918,299 | 11/1975 | Donnadieu | 73/91 |
| 3,983,745 | 10/1976 | Juusola | 73/88 |
| 4,003,246 | 1/1977 | Cain | 73/90 |
| 4,175,447 | 11/1979 | Fukuhara | 73/799 |
| 4,418,563 | 12/1983 | Kalthoff et al. | 73/12 |
| 4,574,642 | 3/1986 | Fleischman | 73/799 |

FOREIGN PATENT DOCUMENTS

| | | |
|---|---|---|
| 58-211626 | 9/1983 | Japan . |
| 2057124 | 3/1981 | United Kingdom . |
| 2108684 | 5/1983 | United Kingdom . |

OTHER PUBLICATIONS

Production of Maximum Sharpeness Stress Concentration Notches in Cylindrical Specimens by Burnos, et al., Zav. Lab., vol. 38, No. 2, p. 242 (2/72).

Primary Examiner—Jerry W. Myracle
Attorney, Agent, or Firm—T. P. Lewandowski; Thomas E. Kocovsky, Jr.

[57] ABSTRACT

A sample (16) with a cut (18) is mounted by clamps (14) between a stationary bar (10) and a movable bar (12). A motor driven cam (22) reciprocates the movable bar causing the samples to undergo cyclic deformation. A camera (C) is selectively positionable (B) to view each of the plurality of samples. A computer control (D) determines a cut length (60, 62, 64, 66) from each two dimensional electronic video image representation and stores it in a cut data memory (68). The next sampling time for each sample is calculated (72) generally in proportion to an inverse of the cut growth rate. The sampling order is re-ordered after each measurement and stored in a queuing table (78). A driver circuit (86) causes a motor (40) to position the camera in the appropriate positions to image the samples in the order indicated by the queuing table.

19 Claims, 4 Drawing Sheets

MULTIPLE SAMPLE AUTOMATED CUT GROWTH ANALYSIS

BACKGROUND OF THE INVENTION

The present invention relates to the automated material analysis arts. It finds particular application in conjunction with the automatic measurement of cut growth in rubber and will be described with particular reference thereto. However, it is to be appreciated that the invention may also find application in conjunction with other kinds of crack testing, flex testing, and other kinds of failure testing in rubber, elastomers, and other materials.

Heretofore, cut growth measurements were commonly made manually. That is, a plurality of rubber samples were mounted at their opposite ends to a pair of parallel bars. One of the bars was reciprocated such that the rubber samples were cyclically stretched. Periodically, e.g. every four hours, the cyclic stretching was stopped and the length of each cut was measured manually, typically with an optical microscope.

One of the problems with this procedure was that manual measurement was relatively slow. When a large number of samples were tested concurrently, e.g. two dozen samples, the manual cut measurements could take a couple hours.

Another problem with this manual technique is that the cyclic rubber deformation was stopped during the manual cut measurements, as well as at night and over weekends. The long pauses in the cyclic elongation raised questions regarding whether the rubber samples were to relax sufficiently that viscoelastic effects altered the test results.

Commonly, the cuts grew very slowly, if at all, for a long period, typically many days. Once a cut started to grow, failure could occur quickly, e.g. overnight. Accordingly, the tests could not be allowed to run unattended, absent the continuous presence of laboratory personnel. Moreover, the relatively long intervals between measurements were reduced as failure started to occur. These shorter time interval samplings could be every hour or even twenty minutes or less. Because the plurality of samples were flexed concurrently, it was necessary to stop the flexing of all samples while the failing sample was measured more frequently.

One attempt to automate the test procedure is illustrated in U.S. Pat. No. 4,574,642, issued Mar. 11, 1986. One drawback of the disclosed test apparatus is that it tested only a single rubber sample. Because the test apparatus could only test one sample at a time, the test cost per sample was relatively high. This apparatus utilized a line scan camera, i.e. a single linear array of photodiodes to monitor cut length. More specifically, the cut length was determined by integrating the output of the illuminated diodes. The resultant analog voltage signal had an amplitude varied in accordance with the number of photodiodes illuminated by light passing through the cut. The use of a one dimensional array limited the measurement to relative cut length rather than length of the cut relative to the width of the sample.

The analog voltage signal oscillated as the sample stretched and contracted. Although each voltage peak was indicative of cut length, inherent voltage drift rendered the peaks inaccurate as a measure of absolute length.

The present invention provides a new and improved analysis system and technique which overcome the above referenced problems and others.

SUMMARY OF THE INVENTION

In accordance with the present invention, a testing apparatus is provided for concurrently performing deformation tests on a plurality of samples. A cyclic deforming means cyclically deforms the plurality of samples. A video camera selectively forms image representations of each sample. A positioning means selectively positions the camera and each sample in a preselected relationship such that the camera successively views and forms images of each sample. A control means receives the image representation from the camera, analyzes them and controls the positioning means in accordance therewith.

In accordance with another aspect of the present invention, a method is provided for concurrently performing deformation tests on a plurality of samples. The samples are cyclically deformed. A video camera is selectively positioned in a preselected relationship with each sample such that the camera successively views each sample. Image representations are formed of each viewed sample. The image representations are analyzed and the repositioning of the camera is controlled in accordance with the image analysis.

One advantage of the present invention is that it enables a multiplicity of samples to be tested concurrently.

Another advantage of the present invention is that it requires little manual labor and is cost effective.

Yet another advantage of the present invention is that test measurements are made on the fly. This expedites completion of the analysis process and eliminates any viscoelastic transient effect errors in the results.

Still further advantages of the present invention will become apparent upon reading and understanding the following detailed description.

BRIEF DESCRIPTION OF THE DRAWINGS

The invention may take form in various steps and arrangements of steps and in various components and arrangements of components. The drawings are only for purposes of illustrating a preferred embodiment and are not to be construed as limiting the invention.

DETAILED DESCRIPTION OF THE PREFERRED EMBODIMENT

Figure 1:
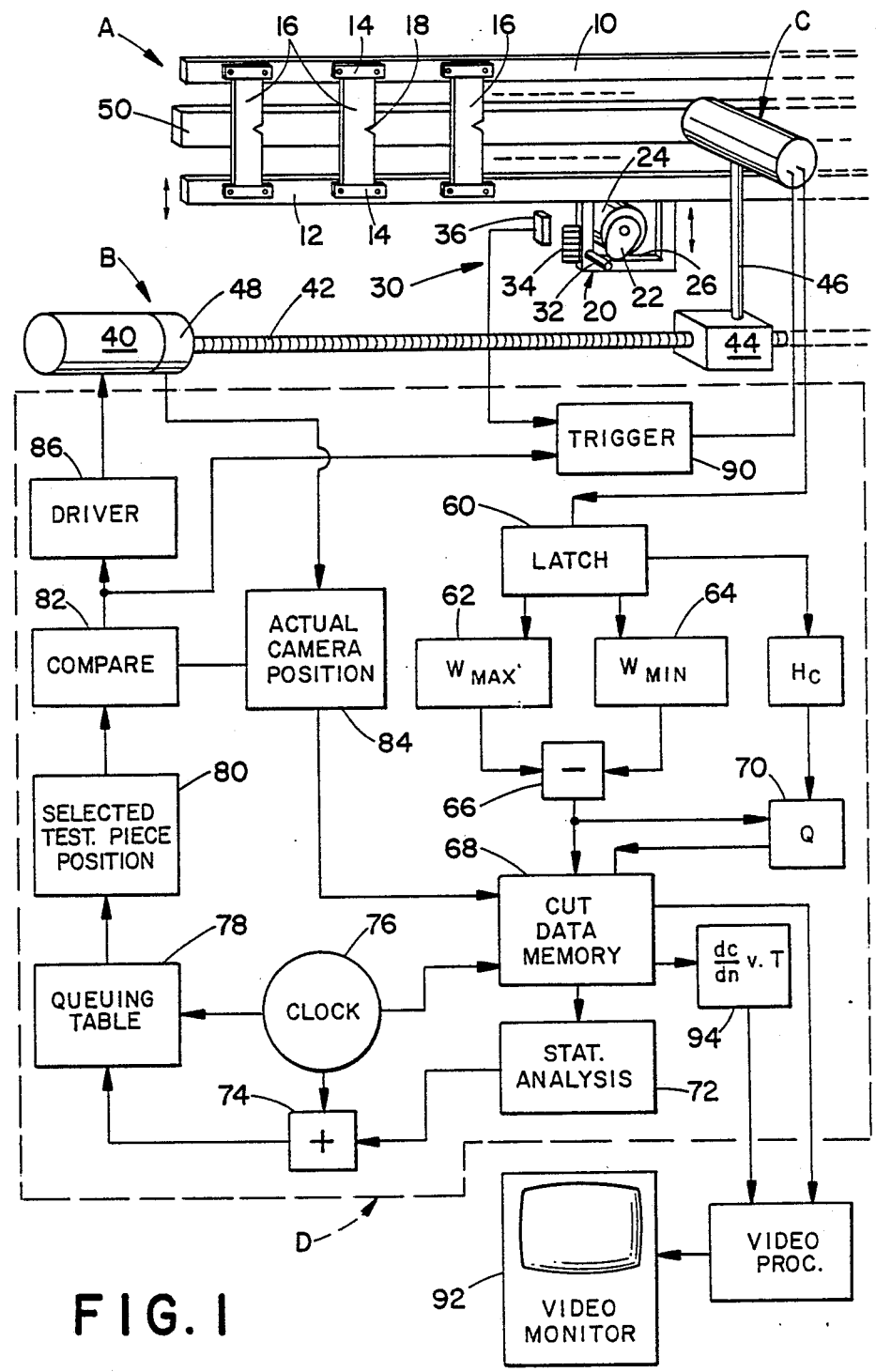
FIG. 1 is a diagrammatic illustration of a test apparatus in accordance with the present invention.

With reference to FIG. 1, a cyclic deforming means A cyclically stretches or otherwise deforms each of a plurality of samples mounted at test stations therealong. A positioning means B selectively positions a video camera or other opto-electric camera means C in a position to view the sample at each test station. A computer based control means D receives and stores data from the camera concerning the test sample at each test station. The control means further analyzes the test data to determine an optimal sampling order and controls the positioning means B accordingly.

The cyclic deforming means A includes a stationary mounting bar 10 and a movable mounting bar 12. Test sample mounting means such as clamps 14 mount one end of each test piece or sample 16 to the stationary bar and another end to the movable bar. In the preferred embodiment, the test sample is a strip of rubber or other elastomer with an initial cut 18.

A reciprocating means 20 cyclically moves the movable bar 12 relative to the stationary bar such that each mounted sample is deformed, and stretched in the preferred embodiment. A cam 22 is rotated by an electric or pneumatic motor 24. The cam engages a surface 26 associated with the movable bar causing the bar to be moved downward against the spring force of the mounted rubber samples. Preferably, a spring is provided for returning the movable bar to an initial or rest position in the absence or rubber samples.

A deformation sensing means 30 senses the amount that the sample is deformed. In the illustrated embodiment, the deformation sensing means includes a light source 32 which transmits a defined beam of light through a graticule 34 to a light sensing means 36, such as a pair of diodes. By counting the number of graticule marks that break the light beams and the order in which the marks shadow the two diodes, the exact position of the movable bar, hence the degree of stretching or displacement of the samples, is measured.

Other degree of deformation or stretching sensors may alternately be provided. When the samples are only measured or analyzed when they are at their maximum stretch positioning, the deformation sensor need only sense when the movable bar is at the corresponding extreme of movement. This can be done with a mechanical sensor, such as an adjustably positionable limit switch, an LDVT, other types of optical sensors, a magnetic and reed switch arrangement, or the like for detecting the position of the movable bar 12. As yet another alternative, the position of the cam 22 may be monitored. The cam itself may be monitored either optically or mechanically, or a rotational position encoder on the shaft of the motor 24 can provide an indication of when the cam has forced the movable bar to the appropriate extreme of motion.

The positioning means B includes an electric motor 40 which rotates a screw 42 which drives a follower 44 along an axis parallel to the bars 10, 12. The video camera C is mounted to the follower 44 by an extension 46 to position the camera such that it selectively focuses on a region of each test sample adjacent the cut. A relative position measuring means 48, such as an annular position encoder measures the position of the camera along the longitudinal axis. That is, from the number of rotations of the screw 42, the direction of rotation, and the pitch of the threads, the position of the follower 44, hence the video camera C is accurately determined.

Other positioning means may, of course, be provided, For example, the follower may be moved by a pneumatic or hydraulic extensible ram, by a belt or chain, with servo motors, or the like. Moreover, a vertical positioning means may be provided along support 46 for selectively raising and lowering the position of the video camera. For example, a second bank of sample mounting rods may be mounted above or below the illustrated bank. The second bank of samples may be interconnected to be reciprocated by motor 24 or may include a second reciprocating means. The camera may, thus, be positioned both axially and vertically to accommodate the two dimensional array of samples.

The video camera C has a two dimensional array of image sensing elements such as CCD's or other diodes. Light passing through the cut 18 from an illuminating means 50 is focused by the camera lens on the two dimensional sensor array. With the backlit embodiment in the preferred embodiment, the camera sees either white light passing through the cut or black shadow where the sample is intact. No gray scales are necessary. Accordingly, the sensor array is configured and biased such that the output from each element of the array assumes one of only two states, (i) zero or black and (ii) one or white. With backlighting provided by a standard fluorescent tube and two 128×256 arrays, the image is acquired in about 10 milliseconds. However, the exposure time may be selected in accordance with the stretching speed, the lighting intensity, camera sensitivity, and the like to reduce the exposure time as to short as one millisecond. This enables the cut length to be captured at the point of maximum sample extension.

Figure 2:
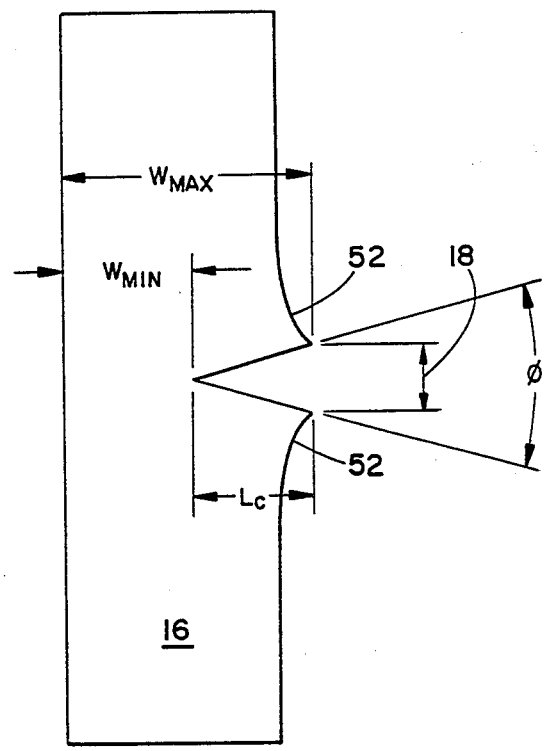
FIG. 2 is a planar view of a rubber test sample to illustrate measurements taken in accordance with the present invention.

With reference to FIG. 2, each sample 16 is precut at 18 substantially a selected distance. The sample has a rest width $W_o$ before being cut and at regions away from the cut, e.g. 25 mm. The sample has a minimum width $W_{min}$ at the cut which width decreases as the cut increases in length. Adjacent the cut, the width of the sample flares out in small lips 52 such that the sample has a width $W_{max}$. The applicants determine the cut length $L_c$ by subtracting the minimum width $W_{min}$ from the maximum width $W_{max}$, i.e.:

$$L_c = W_{max} - W_{min} \tag{1}$$

The two dimensional array of the video camera C is arranged such that video signal or data lines of pixel values extend parallel to the widths $W_{min}$ and $W_{max}$. The line of the image which has the most white or fully illuminated pixels is the line which represents $W_{min}$ and the line with the largest number of black pixels is the line which represents the dimension $W_{max}$. The control means D includes an appropriate temporary storage memory 60 to receive each image representation. A maximum width determining means 62 determines $W_{max}$ and a minimum width determining means 64 determines $W_{min}$. A subtracting means 66 performs the subtraction of Equation (1) and stores the resultant cut length in a cut length memory 68 in conjunction with a sample identification and a sampling time or cycle.

A cut angle determining means 70 measures the angle $\phi$ of the cut. The vertical column of pixel values from the temporary image memory 60 which intersects the lips 52 is determined. The distance between the two lips is measured to determine the cut height $H_c$. Using standard trigonometric relationships, the cut angle $\phi$ is readily calculated. For example, the tangent of half the cut angle is equal to the ratio of half of the cut height divided by the cut length, i.e.

$$\tan(\phi/2) = H_c/L_c \tag{2}$$

A sampling interval means 72 determines the next sampling time for each sample in accordance with the rate at which the length of each sample cut is growing. For example, a statistical analysis means may divide the time between the two most recent images of a given sample by a change in the cut length to determine an inverse of the rate of cut expansion. The sampling interval for that sample is proportional to the inverse of the cut expansion rate. For example, the sampling interval may be set at the shorter of two hours or the time for the sample to grow one tenth millimeter.

An adding means 74 adds this sampling interval to the current time from a clock means 76 and the next sampling time for the given sample is stored in a queuing table 78. The clock means 76 addresses the queuing table 78 and the cut length memory 68. Optionally, the clock means may be a counter that counts the number of cycles of cyclic deforming means. The queuing table stores the time at which each test piece is next scheduled to be sampled. In the preferred embodiment, the queuing table is initialized at the beginning of a test run such that each sample is examined about two hours after test initiation. As the cut expands, progressively shorter times are loaded into the queuing table and are sorted in time order.

As the sampling time for the next sample is reached, its position is loaded into a next sample register 80. A comparing means 82 compares the next sample position from the next sample register 80 with the camera position from a camera position register 84 as determined by the positioning coder 48. The camera position register is connected with the cut length memory to provide it with sample identification data. A motor driver 86 causes the motor 40 to turn the screw 42 until the camera C is in the selected position.

When the comparing means 84 determines that the camera is in the selected position and when the deformation sensing means 30 determines that the sample is in the maximum stretched position, a triggering means 90 is enabled which causes the camera C to take an image of the sample. The above described analysis procedure is then repeated until all samples have been tested to failure.

Figure 3:
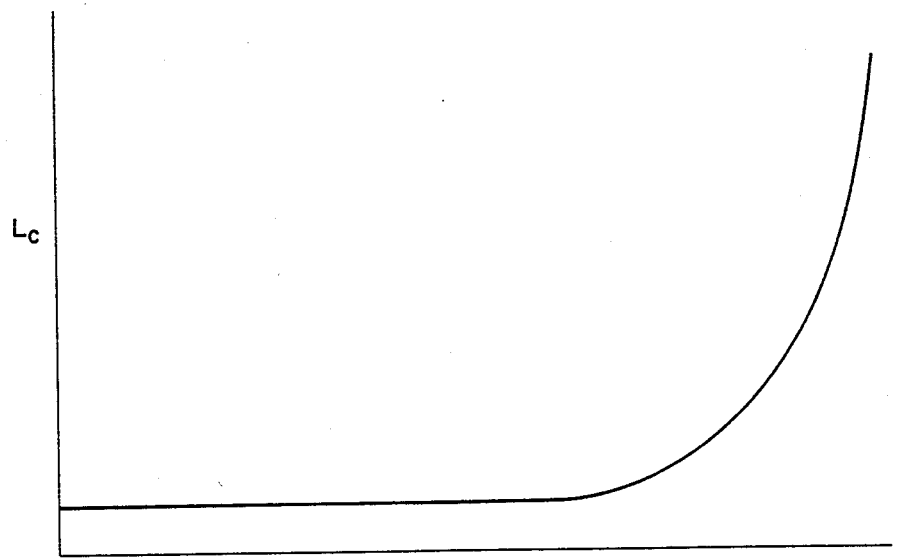
FIG. 3 illustrates a typical cut length vs. number of cycles (time) of samples tested on the apparatus of FIG. 1; and, FIG. 4 is a computer flow chart for a preferred software implemented control of the hardware of FIG. 1.

With reference to FIG. 3, in rubber samples, the cut length $L_c$ commonly grows very slowly, if at all, for a relatively long duration. A good rubber composition for off road vehicle tires commonly lasts a week or two in this slow growth period. Eventually, the cut length starts increasing progressively more rapidly. Commonly, a rubber sample will go through the entire rapid acceleration period within half a day. During the slow growth rate period, sampling intervals of about two hours are acceptable. The sampling time is accelerated as the rate of cut length accelerates to twenty minutes or less. Traditionally, sampling is terminated when the cut has extended to about half of the sample width.

The selected information stored in the cut length memory 68 is displayed on appropriate video monitor 92 or other man readable display. The raw data may be displayed, as well as graphs analogous to FIG. 3. A dc/dn curve means 94 calculates the data points for a graphic display of the rate of cut growth vs. tensile strength, which is proportional to cut length for the tensile test pieces of the preferred embodiment.

Figure 4A:
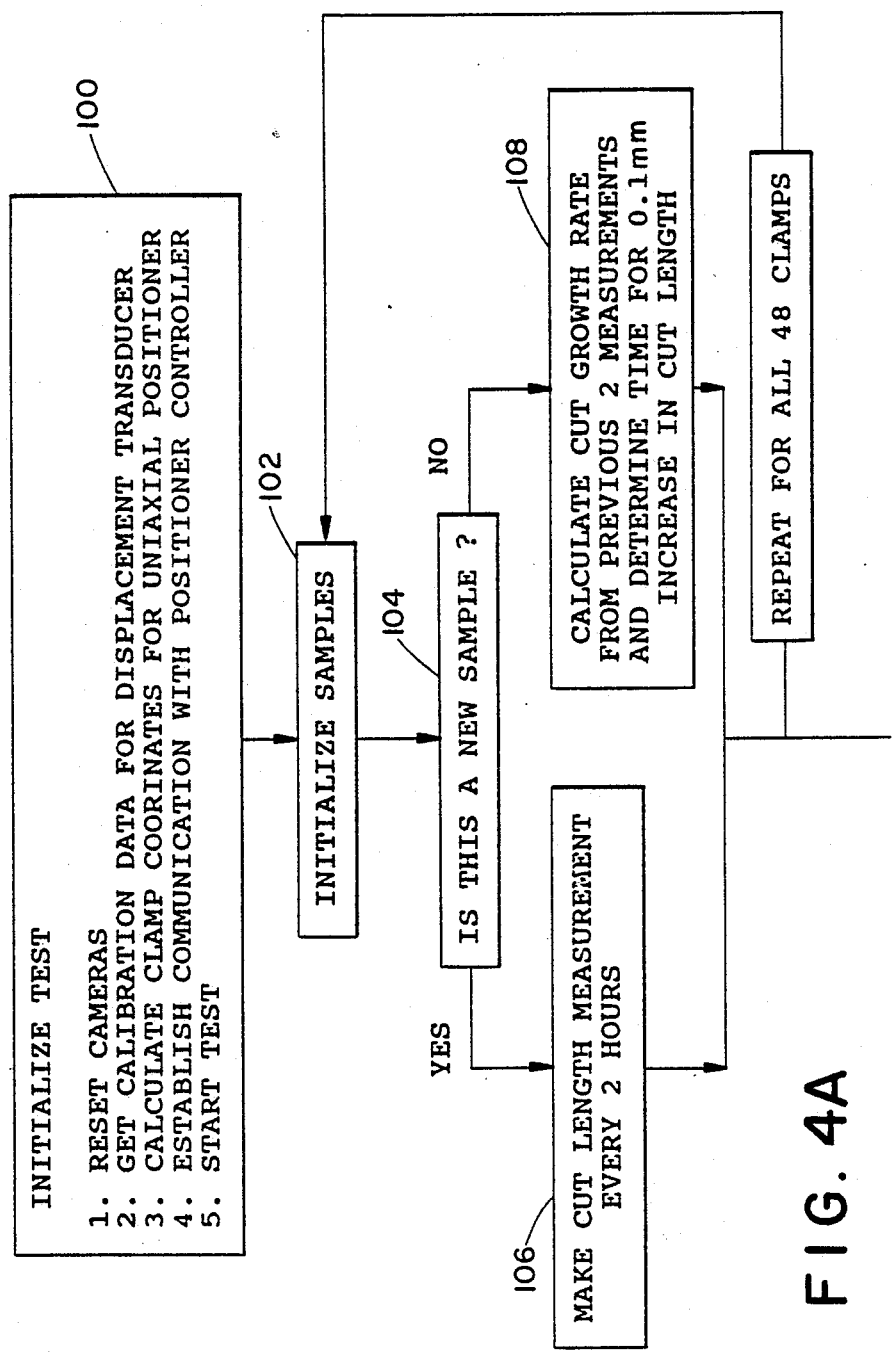
Figure 4B:
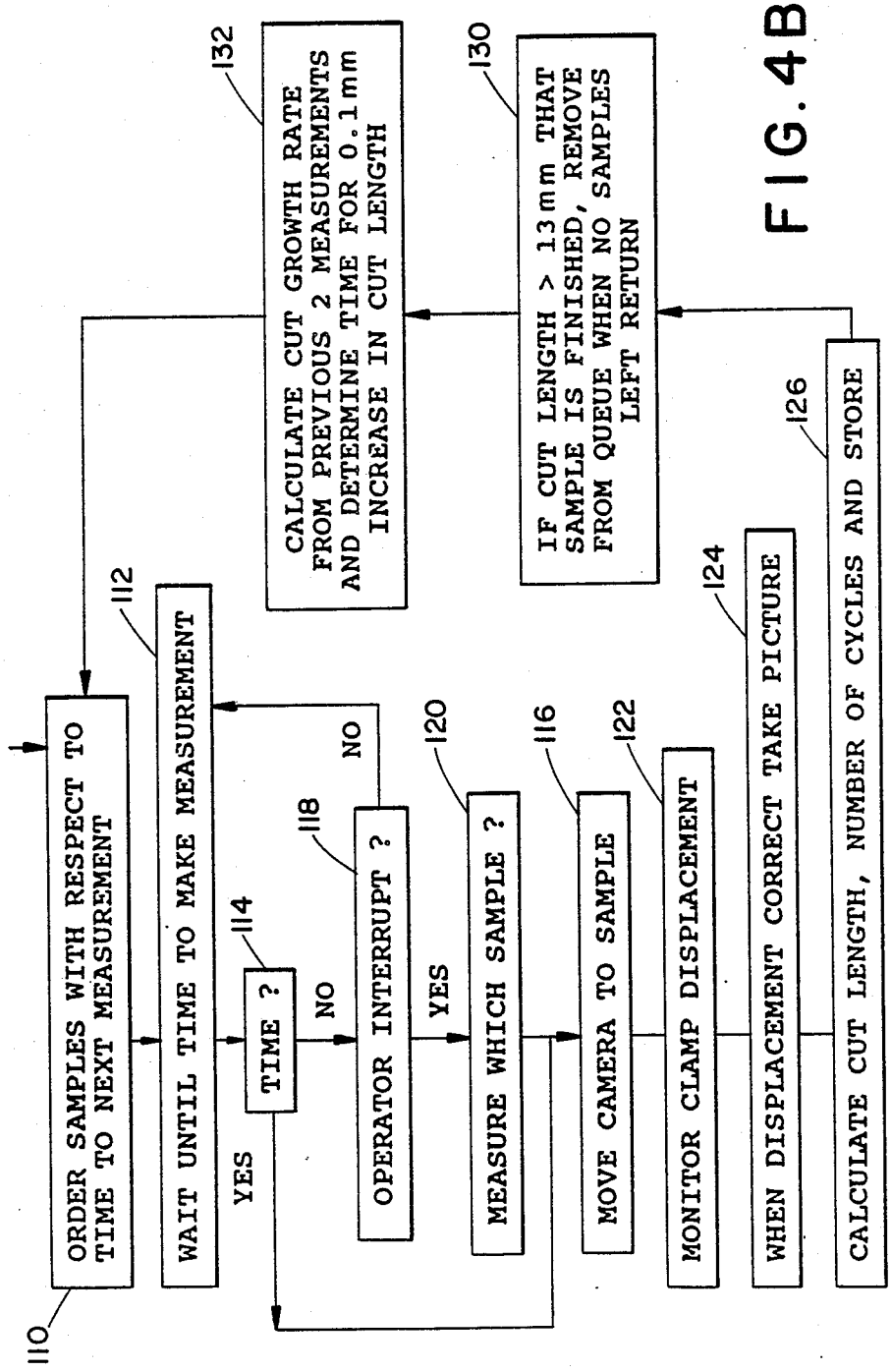

With reference to FIG. 4, the data storage and analysis of the control means D are preferably performed in the software of an appropriately programmed computer. To calibrate the system, an operator enters at 100 header information into the memory 68. That is, for each test position, the operator enters appropriate information about the mounted test piece. The operator further calibrates the displacement transducers 30, the preselected camera positions, and an initial position for the camera, and the like. At a step or means 102, the program initializes the samples. At a step or means 104, the system determines whether or not the test piece or sample at a given position is a new sample or one that has been in the test for awhile. Note, that as samples fail, new samples can be added without stopping the test procedure. If the sample is new, then a step or means 106 sets the sampling interval at two hours. If prior measurements have been taken on the sample, a step or means 108 calculates the cut growth rate and projects the time for the cut to grow 0.1 mm.

After the sampling has been completed for all of the samples, 48 samples in the preferred embodiment, a step or means 110 reorders the sample identifications in the queuing table with respect to the projected next sampling time. The program waits 112 until the next sampling time arrives, while comparing at 114 the current time to the next sampling or measuring time. If it is time to image a test piece, a step or means 116 causes the camera to be moved to the appropriate sampling position. Even if it is not time, a step or means 118 determines whether or not an operator has manually overridden the sampling sequence. If the operator has not, the program returns to the step or means 110. If an operator has commanded the testing of a specific sample, then a step or means 120 determines which sample, such that the step or means 116 moves the camera to the appropriate position.

At a step or means 122, the displacement of the bars 10 and 12 as measured by transducer 30 is monitored. When a preselected displacement is reached, a step or means 124 causes the camera to take a picture. At a step or means 126, the program calculates the cut length, the number of cycles (time), and stores the information.

A comparing step or means 130 compares the cut length to 13 millimeters, i.e. half the sample width. If the cut has extended to this length, the sample designation is removed from the queuing table and no more measurements are taken. If the cut length is less than 13 millimeters, then a step or means 132 calculates the growth rate from the previous two cut length measurements and projects a time for the next tenth of a millimeter increase in cut length. This time is communicated to the step or means 110 as the next sampling time for this sample.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A testing apparatus for concurrently performing deformation tests on a plurality of samples, the apparatus comprising:

a cyclic deforming means for cyclically deforming the plurality of samples;

an opto-electric camera for selectively forming electric image representations of a selected sample;

a positioning means for selectively positioning the camera and each sample in a preselected relationship such that the camera successively forms images of each sample;

a control means which receives image representations from the camera, analyzes the image representations and controls the positioning means in accordance therewith.

2. The apparatus as set forth in claim 1 wherein the cyclic deforming means includes a reciprocating means for cyclically stretching elastomeric samples which have a test cut therein, the camera being positioned to view a region of the sample adjacent the cut.

3. The apparatus as set forth in claim 2 wherein:
the camera generates two dimensional image representations, each having a plurality of lines of data; and,
the control means includes a maximum width determining means for determining a line of data in which the sample is widest, a minimum width determining means for determining a length of a line of the data in which the width of the sample is a minimum, and subtracting means for determining the difference in the minimum and maximum widths to determine a cut length.

4. The apparatus as set forth in claim 1 further including a lighting means disposed opposite the samples from the camera such that the lighting means backlights the samples and wherein the camera means generates a two dimensional image representation of each backlit sample in which each pixel of the two dimensional image representation is limited to one of two values.

5. The apparatus as set forth in claim 1 wherein the control means includes:
an analyzing means for analyzing the image representations received from the camera to determine a sampling interval in accordance with a growth rate of a deformation related defect in each sample;
a queuing table means for storing an order in which the camera is to be positioned among the plurality of samples, the queuing table means being operatively connected with the analyzing means and the positioning means.

6. The apparatus as set forth in claim 5 wherein: the samples are strips of rubber having a cut of preselected initial dimension therein; and,
the control means further includes:
a means for determining from each image representation a width of the sample through the cut and a width of the sample displaced from the cut,
a subtraction means for subtracting the widths to determine a cut length; and,
the analyzing means includes means for determining a ratio of a change in cut length to a difference in time between the corresponding image representations.

7. The apparatus as set forth in claim 1 wherein the cyclic deforming means includes a reciprocating means for reciprocating one end of each sample and further including a displacement sensing means for sensing reciprocating displacement, the displacement sensing means being operatively connected with a trigger means for triggering the camera to produce the two dimensional image representation at a preselected displacement, whereby all images are created with the same degree of sample deformation.

8. The apparatus as set forth in claim 1 wherein:
each sample is a strip of rubber having a cut therein;
the camera produces a two dimensional image representation of a region of each sample adjacent the cut; and,
the control means includes an analysis means for analyzing the two dimensional image representation to determine an angle of the cut.

9. An automatic, multistation failure testing apparatus for measuring cut growth of cut tensile elastomeric test pieces, the apparatus comprising:
a reciprocating means for cyclically stretching and relaxing concurrently each of a plurality of the test pieces;
a means for measuring reciprocation displacement;
a two dimensional opto-electric camera for generating an electronic two dimensional image representation of each test piece, the camera being operatively connected with the displacement sensing means to transmit the image representation at a preselected displacement;
a positioning means for selectively positioning the camera to view each of the plurality of test pieces;
a control means including:
a means for calculating cut lengths from the image representations,
a memory means for storing each calculated cut lengths in conjunction with indication of sampling times and test piece identifications,
a means for calculating a next sampling time for each test piece based on a rate of cut size increase calculated from information stored in the memory means,
a queuing means for storing an order in which the camera is to view the test pieces in accordance with the calculated next sampling times,
a driver means for causing the camera positioning means to move the camera to view the next test piece indicated by the queuing means.

10. A method of measuring cut growth in cut tensile elastomeric work pieces, the method comprising:
cyclically stretching and relaxing each of a plurality of the test pieces concurrently;
selectively positioning an opto-electric camera to view each of the plurality of test pieces;
generating an electronic two dimensional image representation of each test piece at a preselected reciprocation displacement;
calculating a cut length from the image representations;
storing each calculated cut length in conjunction with an indication of sampling time and a test piece identification;
calculating a next sampling time for the camera to generate the two dimensional electronic image representation of each test piece based on a rate of cut length increase;
repositioning the camera to view the test pieces in order in accordance with the calculated next sampling times.

11. A method for concurrently performing deformation tests on a plurality of samples, the method comprising:
cyclically deforming the plurality of samples;
selectively positioning an opto-electric camera in a preselected relationship with each sample such that the camera successively views each sample;
selectively forming image representations of each viewed sample;
analyzing each image representation and repositioning the camera in accordance therewith.

12. The method as set forth in claim 11 wherein the samples are elastomeric and each has a test cut therein and wherein the cyclic deforming step includes cyclically stretching the samples.

13. The method as set forth in claim 12 wherein the camera generates a two dimensional image representation of a region of each sample adjacent the cut.

14. The method as set forth in claim 13 further including analyzing the two dimensional image representation to determine maximum and minimum widths of the viewed region of the sample and determining a difference in the determined maximum and minimum widths.

15. The method as set forth in claim 11 wherein the video camera generates a two dimensional image representation composed of a plurality of data elements which are limited to one of two values.

16. The method as set forth in claim 11 wherein the analyzing step includes determining a sampling interval in accordance with a growth rate of a deformation related defect in each sample and further including repositioning the camera to view the samples in accordance with the relative determined defect growth rates.

17. The method as set forth in claim 16 wherein the samples are strips of rubber each having a cut of preselected initial dimension, the deformation related defect growth rate being a growth rate of the cut, such that the camera is repositioned to view each sample at time intervals which are generally inversely proportional to the cut growth rate.

18. The method as set forth in claim 11 wherein the cyclic deforming step includes cyclically displacing one end of each sample while monitoring a degree of reciprocating displacement and further including initiating the step of forming an image representation in response to monitoring a preselected degree of reciprocating displacement, whereby the images are each created with the same degree of sample deformation.

19. The method as set forth in claim 11 wherein the samples are elastomeric and each has a cut therein and wherein the analyzing step further includes analyzing each two dimensional image representation to determine an angle of the cut.

* * * * *